United States Patent [19]

Hochstein

[11] Patent Number: 4,635,473
[45] Date of Patent: Jan. 13, 1987

[54] OIL DEGRADATION AND TEMPERATURE MONITOR

[76] Inventor: Peter A. Hochstein, 2966 River Valley Dr., Troy, Mich. 48098

[21] Appl. No.: 794,463

[22] Filed: Nov. 4, 1985

[51] Int. Cl.$^4$ .................................................. G01M 19/00
[52] U.S. Cl. ..................................................... 73/118.1
[58] Field of Search .................. 73/118, 304 R, 304 C, 73/292; 123/196 S; 184/6.22, 6.4; 340/620, 59, 618, 622; 374/144, 142; 324/65 P

[56] References Cited

U.S. PATENT DOCUMENTS

| | | | |
|---|---|---|---|
| 2,122,578 | 7/1938 | McMaster et al. | 324/65 P |
| 3,477,290 | 11/1969 | Lerner | 73/292 |
| 3,499,130 | 3/1970 | Norred | 73/304 R |
| 3,735,638 | 5/1973 | Miller | 73/304 R |
| 4,027,534 | 6/1977 | Zimmermann | 73/304 R |
| 4,296,472 | 10/1981 | Sarkis | 73/304 C |
| 4,467,134 | 8/1984 | Pustell | 374/144 |
| 4,570,483 | 2/1986 | Sobue | 73/118 |

FOREIGN PATENT DOCUMENTS 2718295 10/1978 Fed. Rep. of Germany .... 73/304 R

Primary Examiner—Stewart J. Levy
Assistant Examiner—Robert R. Raevis
Attorney, Agent, or Firm—Harold W. Milton, Jr.

[57] ABSTRACT

An oil monitor assembly (10) comprising a support (12) for removable attachment to an oil reservoir, a first electrode (14) extending from the support (12) for immersion in an oil in the reservoir and a second electrode (18) extending from the support (12) in spaced relationship to the interior of the first electrode (14). An electrical insulation (22) spaces the second electrode (18) within the first electrode (14) at the distal ends and presents a surface (24) in a plane facing the support (12). Perforations (16) in the first electrode are spaced circumferentially thereabout and axially therealong with some of the perforations (16) overlapping the plane of the surface (24) of the insulation (22) and extending toward the support (12) to prevent retention of oil within the first electrode (14) on the surface (24). A temperature sensor (26) is disposed within the second electrode (18). A heat-conducting potting material (28) fills the initiator electrode (18) and encapsulates the temperature sensor (26) and has a radial thickness of at least one tenth the radial spacing (20) of the second electrode (18) within the first electrode (14) to produce a sufficient resistivity for preventing current flow from the oil to the temperature sensor (26).

24 Claims, 2 Drawing Figures

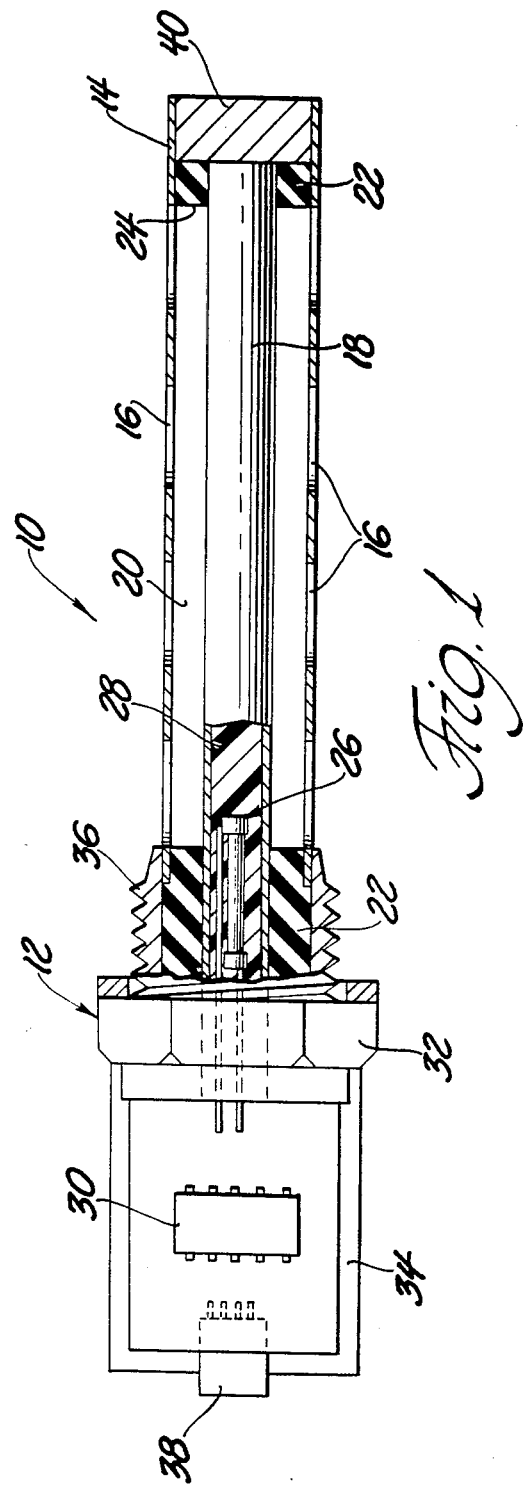
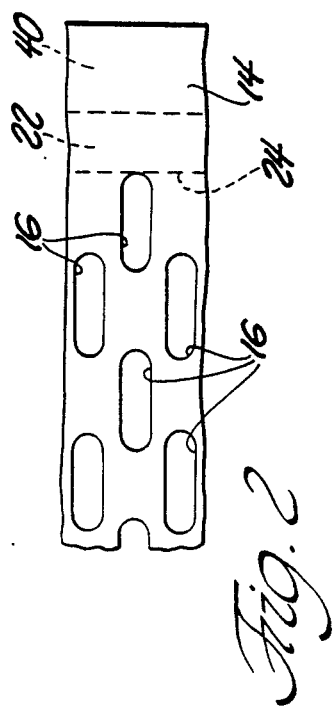

OIL DEGRADATION AND TEMPERATURE MONITOR

TECHNICAL FIELD

This invention relates to monitoring of automotive engine and transmission oil to provide signals at predetermined oil conditions.

BACKGROUND OF INVENTION

Oil monitor sensors have been used for determining the degradation of motor oil by measuring the decrease in resistivity of the oil. This has been accomplished by a motor oil assembly comprising a support member having an outer electrode extending from the support member for immersion in oil in the reservoir having perforations spaced axially therealong. An inner electrode is coaxially disposed within and spaced from the outside electrode with electrical insulation spacing the inner electrode within the outer electrode at the distal ends to present a surface in a plane facing the support member. Oil enters through the perforations of the outer electrode and fills the space between the outer and inner electrodes. An electrical circuit is in direct and immediate electrical contact with the electrodes measuring the resistivity of the oil therebetween. Also, a temperature-sensitive sensor is supported by the support member disposed within the inner electrode encapsulated by heat-conducting potting material for sensing the temperature of the oil.

Unless the perforations are specifically spaced and positioned, the assembly will produce a false reading when removed from the oil reservoir. Thus, the oil monitor may be incorrectly calibrated due to the retained oil, and will produce incorrect measurements when reinserted into the oil reservoir. In addition, electrical current will especially flow from the oil to the temperature sensor to produce inaccurate temperature measurements.

SUMMARY OF THE INVENTION AND ADVANTAGES

An oil monitor assembly comprising; support means for removable attachment to an oil reservoir and a first outer electrode extending from the support means for immersion in oil in the reservoir. A second electrode extends from the support means to a distal end and is in spaced relationship to the first electrode. An electrical insulation means spaces the second electrode within the first electrode at the distal ends and presents a surface in a plane facing the support means. Perforations in the first electrode are spaced circumferentially thereabout and axially therealong with at least one of the perforations extending from at least a position radially aligned with the plane of the surface of the insulation means toward the support means to prevent retention of oil within the first electrode on the surface.

Another feature of the invention is that a temperature sensing means is disposed within the second electrode and a heat conducting potting material encapsulates the temperature sensing means with a radial thickness at least one tenth the radial spacing of the second electrode within the first electrode.

Accordingly, the subject invention removably attached to the oil reservoir will prevent oil from being retained on the surface of the electrical insulation means by capillary action. With at least one perforation radially aligned or overlapping the plane of the surface of the insulation, the oil will drain from the space between the electrodes, preventing any retention of oil on the surface of the electrical insulation means. Thus, a false reading will not occur when the oil monitor assembly is removed from the oil reservoir. Further, this will prevent the oil monitor from being incorrectly calibrated due to the absence of any retained oil. Further, the larger radial thickness of the heat encapsulating potting material will produce a sufficient resistivity for preventing current flow from the oil to the temperature-sensitive sensor.

FIGURES IN THE DRAWINGS

Other advantages of the present invention will be readily appreciated as the same becomes better understood by reference to the following detailed description when considered in connection with the accompanying drawings wherein:

FIG. 1 is a side elevational view partially broken away and in cross section of an oil monitor assembly constructed in accordance with the instant invention;

FIG. 2 is a fragmentary plan view of an electrode for use in the assembly of FIG. 1.

DESCRIPTION OF THE PREFERRED EMBODIMENT

An oil monitor assembly constructed in accordance with the subject invention is generally shown at 10 in FIG. 1. The assembly 10 includes support means, generally indicated at 12, for removable attachment to an oil reservoir. An outer first electrode 14 extends from the support means 12 to a distal end for immersion in oil in the reservoir. An inter second tubular electrode 18 extends from the support means 12 to a distal end and is in spaced relationship 20 to the first electrode 14. An electrical insulation means 22 spaces the second electrode 18 within the first electrode 14 at the distal end and presents a surface 24 in a plane facing the support means 12.

The first electrode 14 is tubular and has perforations 16 spaced circumferentially thereabout and axially therealong with at least one of the perforations 16 extending from at least a position radially aligned with the plane of the surface 24 of the insulation means 22 toward the support means 12 to prevent retention of oil within the first electrode 14 on the surface 24, as illustrated in FIG. 2. In other words, at least one perforation 16, but preferably a plurality of perforations 16, extend from a position coinciding with a plane position radially aligned with or defined by the surface 24 of the insulation means 22 in a direction toward the support means 12 to prevent retention of oil within the first electrode 14 on the surface 24 of the insulation means 22. Thus, preventing the retained oil from producing a false reading when removed from the oil reservoir, although not shown, the perforation 16 may actually extend through and overlap the plane of the surface 24.

The assembly 10 also includes temperature-sensing means, generally indicated at 26, and disposed within the second electrode 18. A heat-conducting potting material 28 fills the electrode 28 and encapsulates the temperature-sensing means 26. The heat-conducting potting material 28 has a radial thickness from the longitudinal axis of the second electrode 18 at least one tenth or greater than the radial spacing 20 of the second electrode 18 within the first electrode 14, thereby producing a sufficient resistivity for preventing current flow from electrode 18 to the temperature-sensing means 26. In other words, the radial thickness of the heat-conducting potting material 28 has to be great enough to produce a sufficient resistivity to prevent electrical current flowing from the oil to the temperature sensing means 26, producing an incorrect signal.

The assembly 10 also includes an electrical circuit means 30 of the type disclosed in copending U.S. application Ser. No. 723,809 in the name of Peter A. Hockstein.

The support means 12 includes a nut 32 and a housing 34 attached to one side of the nut 32 and a threaded skirt 36 extending from the other side of the nut 32. Electrical insulation means 22 is disposed between the skirt 36 and the second electrode 18. The first electrode 14 is supported within and extends from the skirt 36. A second electrical insulation means 22 is disposed annularly between the first and second electrodes 14, 18 at the distal ends thereof. The first or outer electrode 14 is sufficiently perforated to allow oil to enter and exit from the space 20 between the electrodes 14, 18. As illustrated in FIG. 2, the perforations 16 may be elongated, oval, or elliptical holes. In any case, the hole or void area should be at least twenty-five percent (25%) of the total cylindrical surface of the electrode 14. A connector means 38 is disposed on the housing for connection to opposed voltage supplies whereby the support means 12 may be attached to a nonelectrically conductive member. In other words, the reservoir into which the assembly 10 is inserted may be plastic. A magnet means 40 is attached to the end of the first electrode 14 for attracting contaminants in the oil. Specifically, the magnet is disposed within the end of the outer or first electrode 14. The first electrode 14 is made of nonmagnetic and noncorrosive material.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

What is claimed is:

1. An oil monitor assembly (10) comprising; support means (12) for removable attachment to an oil reservoir, a first electrode (14) extending from said support means (12) to a distal end thereof for immersion in an oil reservoir, a second electrode (18) extending from said support means (12) to a distal end thereof and in spaced relationship (20) to said first electrode (14), electrical insulation means (22) disposed annularly between said first (14) and second (18) electrodes and spacing said second electrode (18) within said first electrode (14) at said distal ends and presenting a surface (24) in a plane facing said support means (12), perforations (16) in said first electrode (14) spaced circumferentially thereabout and axially therealong, characterized by at least one of said perforations (16) extending from at least a position radially aligned with the plane of said surface (24) of said insulation means (22) toward said support means (12) to prevent retention of oil within said first electrode (14) on said surface (24).

2. An assembly as set forth in claim 1 wherein said first electrode (14) includes at least one perforation (16) extending through the plane of said surface (24) of said insulation means (22).

3. An assembly as set forth in claim 2 wherein said first electrode (14) is tubular.

4. An assembly as set forth in claim 3 wherein said first electrode (14) has a plurality of said perforations (16) extending from a position radially aligned with the plane of said surface (24) of said insulation means (22) toward said support means (12).

5. An assembly as set forth in claim 4 including temperature-sensing means (26) disposed within said second electrode (18).

6. An assembly as set forth in claim 5 including heat-conducting potting material (28) encapsulating said temperature-sensing means (26) within said second electrode (18).

7. An assembly as set forth in claim 6 wherein said second electrode (18) is tubular.

8. An assembly as set forth in claim 7 wherein said support means (12) includes a nut (32) and a housing (34) attached to one side of said nut (32) and a threaded skirt (36) extending from the other side of said nut (32), said electrical insulation means (22) being additionally disposed between said skirt (36) and said second electrode (18), said first electrode (14) supported within and extending from said skirt (36).

9. An assembly as set forth in claim 8 including electrical circuit means (30) for providing a signal in response to a predetermined temperature sensed by said temperature-sensing means (26) and for providing a signal in the absence of oil between (20) said first (14) and said second (18) electrodes and for providing a signal in response to a predetermined degradation of the oil.

10. An assembly as set forth in claim 9 including a magnet means (40) attached to said first electrode (14) for attracting contaminants in the oil.

11. An assembly as set forth in claim 10 wherein said first electrode (14) is made of nonmagnetic and noncorrosive material.

12. An oil monitor assembly (10) comprising; support means (12) for removable attachment to an oil reservoir, a first electrode (14) extending from said support means (12) to a distal end thereof for immersion in an oil reservoir, a second electrode (18) extending from said support means (12) to a distal end thereof and in spaced relationship (20) to said first electrode (14), electrical insulation means (22) disposed annularly between said first (14) and second (18) electrodes and spacing said second electrode (18) within said first electrode (14) at said distal ends and presenting a surface (24) in a plane facing said support means (12), perforations (16) in said first electrode (14) spaced circumferentially thereabout and axially therealong, temperature-sensing means (26) disposed within said second electrode (18), heat-conducting potting material (28) encapsulating said temperature-sensing means (26) within said second electrode (18) and having a radial thickness radially between said temperature sensing means (26) and the radial periphery of said second electrode (18) at least one tenth the radial spacing (20) of said second electrode (18) within said first electrode (14).

13. An assembly as set forth in claim 12 wherein said heat-conducting potting material (28) is continuous throughout the interior of said second electrode (18) from said support means (12) to said distal end.

14. An assembly as set forth in claim 13 wherein said second electrode (18) is tubular.

15. An assembly as set forth in claim 14 wherein said first electrode (14) is tubular.

16. An assembly as set forth in claim 15 wherein said support means (12) includes a nut (32) and a housing (34) attached to one side of said nut (32) and a threaded skirt (36) extending from the other side of said nut (32), said electrical insulation means (22) being additionally disposed between said skirt (36) and said second electrode (18), said first electrode (14) supported within and extending from said skirt (36).

17. An assembly as set forth in claim 16 including electrical circuit means (30) for providing a signal in response to a a predetermined temperature sensed by said temperature-sensing means (26) and for providing a signal in the absence of oil between (20) said first (14) and said second (18) electrodes and for providing a signal in response to a predetermined degradation of the oil.

18. An assembly as set forth in claim 17 including a magnet means (40) attached to said first electrode (14) for attracting contaminants in the oil.

19. An assembly as set forth in claim 18 wherein said first electrode (14) is made of nonmagnetic and noncorrosive material.

20. An oil monitor assembly (10) comprising; support means (12) for removable attachment to an oil reservoir, a first electrode (14) extending from said support means (12) to a distal end thereof for immersion in an oil reservoir, a second electrode (18) extending from said support means (12) to a distal end thereof and in spaced relationship (20) to said first electrode (14), electrical insulation means (22) disposed annularly between said first (14) and second (18) electrodes and spacing said second electrode (18) within said first electrode (14) at said distal end thereof and presenting a surface (24) in a plane facing said support means (12), temperature-sensing means (26) disposed within said second electrode (18), perforations (26) in said first electrode (14) spaced circumferentially thereabout and axially therealong, characterized by at least one of said perforations (16) extending from at least a position radially aligned with the plane of said surface (24) of said insulation means (22) toward said support means (12) to prevent retention of oil within said first electrode (14) on said surface (24), heat-conducting potting material (28) encapsulating said temperature-sensing means (26) within said second electrode (18) and having a radial thickness radially between said temperature sensing means (26) and the radial periphery of said second electrode (18) at least one tenth the radial spacing (20) of said second electrode (18) within said first electrode (14).

21. An assembly as set forth in claim 20 wherein said first electrode (12) includes at least one perforation (16) overlapping said surface (24) of said insulation means (22).

22. An assembly as set forth in claim 21 wherein said heat conducting potting material (28) is continuous throughout the interior of said second electrode (18) from said support means (12) to said distal end.

23. An assembly as set forth in claim 22 wherein said first electrode (14) has a plurality of perforations (16) extending from a position radially aligned with said surface (24) of said insulation means (22) towards said support means (12).

24. An assembly as set forth in claim 23 wherein said support means (12) includes a nut (32) and a housing (34) attached to one side of said nut (32) and a threaded skirt (36) extending from the other side of said nut (32), said electrical insulation means (22) being disposed between said skirt (36) and said second electrode (18), said first electrode (14) supported within and extending from said skirt (36), electrical circuit means (30) for providing a signal in response to a predetermined temperature sensed by said temperature-sensing means (26) and for providing a signal in the absence of oil between (20) said first (14) and said second (18) electrodes and for providing a signal in response to a predetermined degradation of the oil, and a magnet means (40) attached to said first electrode (14) for attracting contaminants in the oil.

* * * * *